United States Patent
Evans et al.

(10) Patent No.: US 7,153,694 B2
(45) Date of Patent: Dec. 26, 2006

(54) QUANTITATIVE METHOD FOR HYDROCARBON ANALYSIS

(75) Inventors: Knox Alex Evans, Stafford, TX (US); Weijan Mo, Sugar Land, TX (US); Howard Peterson, Houston, TX (US); Ismet Dzidic, Houston, TX (US)

(73) Assignee: Shell Oil Company, Houston, TX (US)

( * ) Notice: Subject to any disclaimer, the term of this patent is extended or adjusted under 35 U.S.C. 154(b) by 416 days.

(21) Appl. No.: 10/304,480

(22) Filed: Nov. 26, 2002

(65) Prior Publication Data

US 2003/0180963 A1    Sep. 25, 2003

Related U.S. Application Data

(60) Provisional application No. 60/334,208, filed on Nov. 29, 2001.

(51) Int. Cl.
*G01N 33/22* (2006.01)
*G01N 33/26* (2006.01)
*G06F 19/00* (2006.01)

(52) U.S. Cl. ................. 436/139; 436/60; 436/140; 436/141; 436/142; 436/143; 436/161; 436/173; 436/181; 700/271; 700/272; 702/23; 702/25

(58) Field of Classification Search ............... 436/60, 436/139–143, 161, 173, 181; 700/266, 271–272; 702/22–25
See application file for complete search history.

(56) References Cited

OTHER PUBLICATIONS

Gallegos, E. J. et al, Analytical Chemistry 1974, 46, 157-161.*
Dunn, W. J., III et al, Environmental Science and Technology 1989, 23, 1499-1505.*
Heberger, K. Analyst 1990, 115, 725-729.*
Dzidic, I. et al, Analytical Chemistry 1992, 64, 2227-2232.*
Villalanti, D. C. et al, Chemical Abstracts 1993, 118, abstract 194779.*
Sellier, N. et al, Journal of Mass Spectrometry 1997, 32, 723-727.*
Anderson, J. E. et al, Chemical Abstracts 2001, 135, abstract 348368.*
Tanaka, Y. et al, Bulletin of the Chemical Society of Japan 2001, 74, 839-849.*
Lawrey, D. M. G. et al, Analytical Chemistry 1962, 34, 538-542.*
Kumar, P. et al, Fuel 1987, 66, 1036-1045.*
Wadsworth, P. A. et al, Hydrocarbon Processing May 1992, 71, 109-112.*
Anderson, J. E. et al, WEFTEC 2000, Annual Conference & Exposition on Water Quality and Wastewater Treatment, 73rd, Anaheim, CA, United States, Oct. 14-18, 2000, 2978-2987, Publisher: Water Environment Federation, Alexandria, Va.*
Lawrey, David M. G. et al, Analytical Chemistry 1962, 34, 538-542.*
Gallegos, E. J., ASTM Special Technical Publication 1986, 902, 5-26.*
Aczel, T. et al, International Journal of Mass Spectrometry and Ion Processes 1989, 92, 1-7.*
Shiomi, K. et al, Journal of High Resolution Chromatography 1991, 14, 729-737.*
Dan C. Villalanti and Philip A. Wadsworth, "Application of NOISE (Nitric Oxide Ionization Spectrometry Evaluation) GC/MS Analysis to Reformulated Gasolines and Their Blending Components," *Journal of Chromatographic Science*, vol. 31, Mar. 1993, pp. 100-104.

* cited by examiner

*Primary Examiner*—Arlen Soderquist
(74) *Attorney, Agent, or Firm*—Charles W. Stewart; Len Miller

(57) ABSTRACT

A method for quantitative determination of hydrocarbon species in a hydrocarbon sample is disclosed. The method uses Townsend Discharge Nitric Oxide Chemical Ionization Gas Chromatography/Mass Spectrometry.

9 Claims, No Drawings

QUANTITATIVE METHOD FOR HYDROCARBON ANALYSIS

This application claims the benefit of U.S. Provisional Application No. 60/334,208 filed Nov. 29, 2001 the entire disclosure of which is hereby incorporated by reference.

FIELD OF THE INVENTION

The invention relates to the quantitative determination of hydrocarbon species in hydrocarbon samples through the use of Townsend Discharge Nitric Oxide Chemical Ionization (TDNOCI) gas chromatography/mass spectrometry (GC/MS).

BACKGROUND OF THE INVENTION

Traditional methods for the analysis of hydrocarbon samples require lengthy, complicated techniques that often do not provide sufficient information about the samples. Some involve a series of traps and multiple valves or columns (Paraffins, Iso-paraffins, Olefins, Naphthenes and Aromatics or PIONA), lengthy chromatographic programs (Detailed Hydrocarbon Analysis or DHA), and some only give boiling range information (Simulated Distillation or SIMDIST). The PIONA analysis does not accurately speciate some of the heavier components in gasolines (especially in the $C_9$–$C_{12}$ range), due to chromatographic overlapping of compounds and the lack of absolute standards for these species. Detailed Hydrocarbon Analysis (DHA) suffers from some of the same lack of specificity problems, and involves relatively lengthy analyses (up to 2 hours each). While SIMDIST provides accurate information on quantities of hydrocarbons within specific boiling ranges, it does not provide any speciation information on these hydrocarbons. A method is needed to provide quantitative information about complex hydrocarbon mixtures that includes speciation within various boiling point ranges. Such information would be particularly useful in the gasoline range.

Additionally, when using the available analytical techniques as described above, the hydrocarbon sample must first be distilled into a number of cuts. The cuts are then analyzed. This procedure requires:

1) A large quantity of the sample for distillation, that may not be available.
2) Distillation of the sample into multiple cuts
3) Determination of the composition of each cut.

None of the typical compositional methods can provide accurate quantification for the high boiling range cuts (e.g., 204° C.+). It would be useful to provide a method that does not require separate cuts of the sample and one that can provide data for high boiling ranges.

The Townsend Discharge Nitric Oxide Chemical Ionization (TDNOCI) method has been developed and applied to kerosene and diesel range hydrocarbon samples as discussed in "Townsend Discharge Nitric Oxide Chemical Ionization Gas Chromatography/Mass Spectrometry for Hydrocarbon Analysis of the Middle Distillates", I. Dzidic, H. A. Petersen, P. A. Wadsworth, and H. V. Hart, Analytical Chemistry, 1992, 64, pp. 2227–2232, which is hereby incorporated by reference.

Previously, this method was not applicable to gasoline range samples, as it did not provide for quantification or identification of olefinic hydrocarbons, which are commonly present (5–45 wt %) in catalytically or thermally cracked gasoline samples. Additionally, as mentioned above, PIONA and DHA analyses are not as specific as is desired for accurate quantification of heavier components in the gasoline samples. SMIDIST analysis alone does not provide specific hydrocarbon type data.

It would be advantageous to adopt the TDNOCI method for use with gasoline range samples including those with olefin constituents.

SUMMARY OF THE INVENTION

The instant invention relates to a method of operating a calibrated gas chromatograph/mass spectrometer system for analysis of the chemical and physical properties of a complex mixture of hydrocarbons comprising:

introducing a sample of the complex mixture of hydrocarbons into the gas chromatograph to partially separate the mixture into its constituent components;

ionizing the resulting components via Townsend discharge nitric oxide chemical ionization;

introducing the resulting ionized components into the mass spectrometer to produce corresponding mass spectra; and, measuring, from the resulting mass spectra, concentrations of individual hydrocarbon species and structural types within certain boiling ranges.

DETAILED DESCRIPTION OF THE INVENTION

The instant invention provides quantitative information about complex hydrocarbon mixtures that includes hydrocarbon speciation in the boiling range between about 23° C. and about 260° C. by analyzing complex hydrocarbon samples (e.g., gasoline) with a boiling range between about 10° C. and about 705° C.

This method provides the concentrations of hydrocarbon species in a complex hydrocarbon mixture without prior separation by distillation into cuts as well as the distribution of the hydrocarbon species as a function of boiling point. The invention utilizes Townsend Discharge Nitric Oxide Chemical Ionization (TDNOCI) gas chromatography/mass spectrometry (GC/MS). This method has been used in the past for hydrocarbon analysis, but had been unable to determine olefin concentration or structural types. In this type of ionization, unique molecular ions are produced for each of the various hydrocarbon species. Complete chromatographic separation is not attained, but chromatographic separation along with mass separation allow for quantification of the individual species' homologues. Formulas I–III show characteristic ion molecule reactions for the various hydrocarbon types (species).

$$NO^+ + M \rightarrow (M-H)^+ + HNO \qquad (I)$$

$$NO^+ + M \rightarrow M^+ + NO \qquad (II)$$

$$NO^+ + M \rightarrow (MNO)^+ \qquad (III)$$

Since little fragmentation occurs, quantification of molecular ions results in higher sensitivity along with higher specificity. Formula I is most characteristic for saturated hydrocarbons. Formula III predominates for aromatics with some of Formula I and II observed. Olefins show a mixed reaction of I, II and III.

An analysis software and analytical techniques are developed to determine the concentrations of individual hydrocarbon species, which are characterized by carbon number ($C_5$–$C_{15}$) as well as structural type (species). The species include, but are not limited to: n-Paraffins, iso-Paraffins, Cyclics, Branched mono Olefins, Linear mono Olefins, Diolefins, Cyclic Olefins, Cyclic Diolefins, Mono Aromatics, Indane/Indenes, Diaromatics, Dicyclics, and Benzothiophenes/Dibenzothiophenes. In addition, this method further quantifies the above species/carbon # groups within various boiling ranges (e.g., 45–65.5° C., 65.5–98.9° C., 98.9–154° C., 154–182° C., 182–204° C., 204–232° C., and 232+° C.). All of this quantitative information is obtained from a single injection of sample, either distillation cuts, or total liquid product (e.g., overhead samples from catalytic crackers, liquid products from hydrocrackers, or thermal conversion units, etc.).

The instant method is capable of quantifying all of the diverse hydrocarbon species within a typical gasoline range sample within a 30 minute chromatographic analysis, and with the same analysis, provides necessary "SIMDIST type" information. All of this is done with a single injection of sample. This analysis can be done on gasoline range samples, distillation cuts, or total liquid products (44.4–704° C.).

With the invention method, a hydrocarbon sample with a boiling range between about 44.4° C. to about 704° C. can be analyzed and the following information can be obtained:
1) Hydrocarbon species by carbon number for the boiling range between about 44.4° C. to about 260° C. of the hydrocarbon sample;
2) Hydrocarbon species as a function of boiling point for the boiling range between about 44.4° C. to about 260° C. of the hydrocarbon sample;
3) Hydrocarbon species by carbon number in a number of narrow fractions (e.g., 45–65.5° C., 65.5–98.9° C., 98.9–154° C., 154–182° C., 182–204° C., 204–232° C., and 232+° C.)

This method can be routinely applied to the analysis of gasoline (full range) samples, gasoline fractions, and total liquid product samples. In addition, it can be applied to similar hydrocarbon samples (paraffins, olefins, naphtha, etc.) where characterization and quantification by hydrocarbon type is needed.

The new method described here accurately quantifies all hydrocarbon (carbon-hydrogen and some sulfur) species, including olefinic species, contained within gasoline range samples. In addition, it also yields quantitative "simdist" type data for the sample, without the additional cost of a separate SIMDIST analysis. And the need for distillation of the sample into a gasoline range fraction or fractions is eliminated by the ability of this method to analyze total liquid products without prior distillation.

The instant invention will be demonstrated by the following illustrative embodiments which are provided for illustration only and are not to be construed as limiting the invention.

EXAMPLE 1

Initially, the method is calibrated using the standard procedure of the gas chromatograph/mass spectrometer (GC/MS) used for the analysis. A suitable GC/MS instrument is the Varian 1200 system from Varian Analytical Instruments. Table 1 gives a list of standard reference materials and their respective total concentrations used.

TABLE 1

| Boiling Ranges wt % (a) | | | | | | | | |
|---|---|---|---|---|---|---|---|---|
| Boiling Range in deg. C. | 46–65.5 | 65.5–98.9 | 98.9–154 | 154–182 | 182–204 | 204–232 | 232+ | Total |
| QA Gasoline | 7.1 | 18.2 | 36.3 | 16.5 | 10 | 8.4 | 3.5 | 100.0 |
| MWK Gasoline A | 17.5 | 29.5 | 49.2 | 3.8 | 0.0 | 0.0 | 0.0 | 100.0 |
| MWK Gasoline B | 11.5 | 30.5 | 54.3 | 3.7 | 0.0 | 0.0 | 0.0 | 100.0 |
| MWK Gasoline C | 13.3 | 27.2 | 53.6 | 5.9 | 0.0 | 0.0 | 0.0 | 100.0 |
| MWK Gasoline D | 16.5 | 30.5 | 48.5 | 4.5 | 0.0 | 0.0 | 0.0 | 100.0 |

| Combined Species Concentrations in wt % (b) | | | | | | | | | |
|---|---|---|---|---|---|---|---|---|---|
| Standard: | Air Liquide #9913 | Air Liquide #9914 | Air Liquide #9915 | QA GAS 113–450 | AC REF Lot# | MWK A 113–310 | MWK B 113–310 | MWK C 113–310 | MWK D 113–310 |
| Species | 14.35 | 21.11 | 32.52 | 16.70 | 32.94 | 35.34 | 15.84 | 20.96 | 26.56 |
| Paraffin ISO | 0.76 | 1.96 | 3.10 | 3.06 | 8.25 | 3.31 | 1.87 | 1.99 | 2.67 |
| Paraffin Normal | 25.30 | 21.14 | 14.53 | 10.92 | 5.65 | 17.49 | 15.04 | 20.54 | 14.40 |
| Mono Cyclic | 0.95 | 2.60 | 3.66 | 15.13 | 5.28 | 13.86 | 23.92 | 11.17 | 18.42 |
| Mono Olefin Branch | 7.20 | 19.75 | 27.78 | 5.18 | 1.86 | 6.56 | 14.56 | 4.70 | 7.40 |
| Mono Olefin Linear | 0.18 | 0.49 | 0.68 | 2.05 | 0.65 | 0.00 | 0.00 | 0.00 | 0.00 |
| Diolefin | 0.00 | 0.00 | 0.00 | 6.57 | 1.60 | 4.11 | 13.62 | 6.79 | 5.37 |
| Cyclic Olefin | 0.00 | 0.00 | 0.00 | 0.27 | 0.29 | 0.00 | 0.00 | 0.00 | 0.00 |
| Cyclic Diolefin | 50.86 | 31.82 | 16.13 | 31.12 | 38.66 | 19.31 | 15.77 | 33.87 | 25.17 |
| Mono Aromatic Indans | 0.00 | 0.00 | 0.00 | 7.08 | 3.03 | 0.00 | 0.00 | 0.00 | 0.00 |
| Diaromatic | 0.00 | 0.00 | 0.00 | 1.93 | 1.11 | 0.00 | 0.00 | 0.00 | 0.00 |
| Dicyclic | 0.00 | 0.00 | 0.00 | 0.28 | 0.08 | 0.00 | 0.00 | 0.00 | 0.00 |
| Total | 99.60 | 98.87 | 98.40 | 100.29 | 99.40 | 99.98 | 100.62 | 100.02 | 99.99 |

(a) From Simdist data
(b) From PIANO, DHAX, Air Liquide Certified wt %, and AC data Each standard is analyzed repeatedly, under the standard operating conditions as listed in Table 2.

TABLE 2

| Standard Operating Conditions | |
|---|---|
| CTC AS200SE Auto Sampler | |
| Pull-up count | = 10 |
| Rinse Volume | = 8 ul |
| Injection Volume | = 1.5 ul |
| Pull-up speed | = 2.0 ul/sec |
| Air volume | = 1.0 ul |
| Post Injection Delay | = 2.0 sec |
| Solvent Cleaning Cycles | = 12 |
|  | = Methylene Chloride |
| HP 6890 GC Injector | |
| Temp | = 280 deg. C Column |
| Head Pressure | = 14 psig Helium Split |
| Mode | |
| Split Ratio | = 85 |
| Gas Saver on at 1.0 minute | |
| Oven | |
| Initial temp | = 40 deg. C |
| Initial isothermal hold | = 3.1 minutes |
| Sequence 2 temp | = 82 deg. C |
| Rate | = 7.9 deg C/minute |
| Final temp. | = 240 |
| Rate | = 9.9 deg C/minute |
| Final Isothermal hold | = 1.0 minute |
| Transfer Line | |
| Temp | = 300 deg. C |
| Varian 1200 Mass Spectrometer | |
| Scan range | = 66 Daltons to 266 Daltons |
| Scan time | = 0.3 seconds per scan |
| Mode | = Centroid Positive Chemical |
| Ionization | |
| Source Temp | = 120 deg. C |
| Manifold Temp | = 40 deg. C |
| Discharge Ionization | = 1200 volts |

TABLE 2-continued

| Standard Operating Conditions | |
|---|---|
| Electron Multiplier | = 1100 volts |
| Nitric Oxide Source Pressure | = >5.3 torr |

The averaged area percent (normalized to 100%) values for each individual standard along with their respective weight percent values was used to determine slope, intercept, and R2 values for each individual homologue of each individual species (for instance, $C_5$ isoparaffins, $C_7$ branched olefins, $C_7$ linear olefins, etc). The slope and intercept values for these individual homologues of each individual species are then used to calculate concentrations from measured area percent values, according to Formula IV:

$$[(\text{If } (Y\text{-intercept})>0, (Y\text{-intercept}),0))/\text{slope}]=X \qquad (IV)$$

where Y is the area percent and X is the weight percent of a specific species homologue with respective slope and intercept. The selected slope and intercept values for each species homologue are stored within the species program, along with select ions, which are a representative of that particular species homologue. The hydrocarbon sample is then analyzed using the GC/MS as set up for chemical ionization using the TIDNOCI technique. The sample can be injected as a single cut taken from a crude oil or a gasoline sample. The total time per sample is about 30 minutes.

After analysis is complete, the data is further processed. First, the spectra are isotope corrected for the naturally occurring carbon-13 contribution from the lower mass ion. Next, sample calculations are performed and species information calculated.

Sample calculations are performed by determining the areas for each of the individual species homologue retention windows, by plotting the selected ions and integrating the areas under the ion chromatogram. This raw area information is then used to calculate combined area percentage values for all species homologues. Individual species homologues for specified boiling ranges are given in Tables 3–9.

TABLE 3

Individual Species Homologues for Boiling Range 45–65.5° C.

| Species | Carbon Number | Slope | Intercept | Ret Time Window Low | Ret Time Window High | Mass 1 | Mass 2 | Mass 3 | Mass 4 | Mass 5 | Mass 6 | Mass 7 |
|---|---|---|---|---|---|---|---|---|---|---|---|---|
| Paraffin ISO | C5 | 1.09 | 0.016 | 3.15 | 3.35 | 71 | 0 | 0 | 0 | 0 | 0 | 0 |
| Paraffin ISO | C6 | 0.94 | 0.389 | 4 | 4.45 | 85 | 0 | 0 | 0 | 0 | 0 | 0 |
| Paraffin Normal | C5 | 0.00 | 0.005 | 3.4 | 3.5 | 71 | 0 | 0 | 0 | 0 | 0 | 0 |
| Mono Cyclic | C5 | 1.00 | 0.038 | 4.05 | 4.15 | 69 | 0 | 0 | 0 | 0 | 0 | 0 |
| Mono Olefin Branch | C5 | 1.30 | 0.557 | 3.05 | 3.2 | 69 | 70 | 100 | 0 | 0 | 0 | 0 |
| Mono Olefin Branch | C5 | 1.30 | 0.557 | 3.37 | 3.44 | 69 | 70 | 100 | 0 | 0 | 0 | 0 |
| Mono Olefin Branch | C5 | 1.30 | 0.557 | 3.9 | 3.63 | 69 | 83 | 100 | 0 | 0 | 0 | 0 |
| Mono Olefin Branch | C6 | 0.84 | 0.000 | 3.3 | 4.36 | 69 | 70 | 84 | 114 | 0 | 0 | 0 |
| Mono Olefin Linear | C5 | 2.88 | 0.000 | 3.44 | 3.37 | 69 | 70 | 100 | 0 | 0 | 0 | 0 |
| Mono Olefin Linear | C5 | 2.88 | 0.000 | 4.36 | 3.57 | 69 | 83 | 100 | 0 | 0 | 0 | 0 |
| Mono Olefin Linear | C6 | 2.29 | 0.269 | 4.36 | 4.5 | 69 | 83 | 84 | 86 | 114 | 0 | 0 |
| Diolefin | C5 | 2.40 | 0.137 | 3.35 | 3.75 | 68 | 98 | 0 | 0 | 0 | 0 | 0 |
| Cyclic Olefin | C5 | 1.99 | 0.008 | 3.9 | 4.1 | 67 | 0 | 0 | 0 | 0 | 0 | 0 |
| Cyclic Diolefin | C5 | 1.00 | 0.005 | 3.7 | 3.85 | 66 | 0 | 0 | 0 | 0 | 0 | 0 |

TABLE 4

Individual Species Homologues for Boiling Range 65.5–98.9° C.

| Species | Carbon Number | Slope | Intercept | Ret Time Window Low | Ret Time Window High | Mass 1 | Mass 2 | Mass 3 | Mass 4 | Mass 5 | Mass 6 | Mass 7 |
|---|---|---|---|---|---|---|---|---|---|---|---|---|
| Paraffin ISO | C7 | 0.74 | 0.362 | 4.9 | 6.6 | 99 | 0 | 0 | 0 | 0 | 0 | 0 |
| Paraffin Normal | C6 | 0.01 | 0.003 | 4.5 | 4.65 | 85 | 0 | 0 | 0 | 0 | 0 | 0 |
| Paraffin Normal | C7 | 0.04 | 0.014 | 6.6 | 6.9 | 99 | 0 | 0 | 0 | 0 | 0 | 0 |
| Mono Cyclic | C6 | 1.15 | −0.360 | 5 | 5.9 | 83 | 0 | 0 | 0 | 0 | 0 | 0 |
| Mono Cyclic | C7 | 1.02 | 1.114 | 6 | 6.55 | 97 | 0 | 0 | 0 | 0 | 0 | 0 |
| Mono Olefin Branch | C6 | 0.84 | 0.557 | 4.45 | 4.59 | 69 | 83 | 84 | 86 | 114 | 0 | 0 |
| Mono Olefin Branch | C6 | 0.84 | 0.557 | 4.68 | 4.8 | 69 | 83 | 84 | 86 | 114 | 0 | 0 |
| Mono Olefin Branch | C6 | 0.84 | 0.557 | 4.9 | 5 | 69 | 83 | 84 | 86 | 114 | 0 | 0 |
| Mono Olefin Branch | C7 | 0.23 | 0.442 | 4.9 | 6.41 | 86 | 98 | 100 | 128 | 0 | 0 | 0 |
| Mono Olefin Branch | C7 | 0.23 | 0.442 | 6.5 | 6.62 | 86 | 98 | 100 | 128 | 0 | 0 | 0 |
| Mono Olefin Branch | C7 | 0.23 | 0.442 | 6.87 | 7.01 | 86 | 98 | 100 | 128 | 0 | 0 | 0 |
| Mono Olefin Branch | C7 | 0.23 | 0.442 | 7.1 | 7.35 | 86 | 98 | 100 | 128 | 0 | 0 | 0 |
| Mono Olefin Linear | C6 | 2.29 | 0.269 | 4.59 | 4.68 | 69 | 83 | 84 | 86 | 114 | 0 | 0 |
| Mono Olefin Linear | C6 | 2.29 | 0.269 | 4.8 | 4.9 | 69 | 83 | 84 | 86 | 114 | 0 | 0 |
| Mono Olefin Linear | C7 | 0.44 | 0.259 | 6.41 | 6.5 | 86 | 98 | 100 | 128 | 0 | 0 | 0 |
| Mono Olefin Linear | C7 | 0.44 | 0.259 | 6.62 | 6.87 | 86 | 98 | 100 | 128 | 0 | 0 | 0 |
| Mono Olefin Linear | C7 | 0.44 | 0.259 | 7.01 | 7.1 | 86 | 98 | 100 | 128 | 0 | 0 | 0 |
| Diolefin | C6 | 1.02 | 0.016 | 4.55 | 5.5 | 82 | 112 | 0 | 0 | 0 | 0 | 0 |
| Cyclic Olefin | C6 | 1.10 | 0.029 | 5.5 | 5.9 | 81 | 82 | 0 | 0 | 0 | 0 | 0 |
| Cyclic Olefin | C7 | 1.19 | 0.109 | 6.68 | 7.2 | 95 | 0 | 0 | 0 | 0 | 0 | 0 |
| Cyclic Diolefin | C6 | 1.08 | 0.009 | 5 | 6 | 80 | 0 | 0 | 0 | 0 | 0 | 0 |
| Mono Aromatic | C6 | 1.23 | 0.139 | 5.5 | 5.7 | 78 | 108 | 0 | 0 | 0 | 0 | 0 |
| Thiophenes + Benzthio | C4 | 5.00 | 0.020 | 5.6 | 5.72 | 84 | 114 | 0 | 0 | 0 | 0 | 0 |

TABLE 5

Individual Species Homologues for Boiling Range 98.9–154° C.

| Species | Carbon Number | Slope | Intercept | Ret Time Window Low | Ret Time Window High | Mass 1 | Mass 2 | Mass 3 | Mass 4 | Mass 5 | Mass 6 | Mass 7 |
|---|---|---|---|---|---|---|---|---|---|---|---|---|
| Paraffin ISO | C8 | 0.49 | 0.592 | 7.2 | 8.8 | 113 | 0 | 0 | 0 | 0 | 0 | 0 |
| Paraffin ISO | C9 | 0.77 | −0.170 | 9.8 | 11.6 | 127 | 0 | 0 | 0 | 0 | 0 | 0 |
| Paraffin Normal | C8 | 0.10 | 0.015 | 9.35 | 9.6 | 113 | 0 | 0 | 0 | 0 | 0 | 0 |
| Paraffin Normal | C9 | 0.32 | 0.000 | 11.95 | 12.2 | 127 | 0 | 0 | 0 | 0 | 0 | 0 |
| Mono Cyclic | C7 | 1.02 | 1.114 | 7.2 | 7.7 | 97 | 0 | 0 | 0 | 0 | 0 | 0 |
| Mono Cyclic | C8 | 1.08 | 0.623 | 7.2 | 9 | 111 | 0 | 0 | 0 | 0 | 0 | 0 |
| Mono Cyclic | C8 | 1.08 | 0.623 | 9 | 10.5 | 111 | 0 | 0 | 0 | 0 | 0 | 0 |
| Mono Cyclic | C9 | 1.57 | −0.110 | 8.7 | 12.45 | 125 | 0 | 0 | 0 | 0 | 0 | 0 |
| Mono Olefin Branch | C8 | 0.27 | 0.135 | 7.3 | 9.07 | 86 | 100 | 112 | 142 | 0 | 0 | 0 |
| Mono Olefin Branch | C8 | 0.27 | 0.135 | 9.14 | 9.2 | 86 | 100 | 112 | 142 | 0 | 0 | 0 |
| Mono Olefin Branch | C9 | 0.18 | 0.107 | 10 | 11.6 | 86 | 100 | 114 | 126 | 156 | 0 | 0 |
| Mono Olefin Linear | C8 | 0.90 | −0.048 | 9.07 | 9.14 | 69 | 83 | 86 | 100 | 112 | 114 | 142 |
| Mono Olefin Linear | C8 | 0.90 | 0.048 | 9.2 | 10 | 69 | 83 | 86 | 100 | 112 | 114 | 142 |
| Mono Olefin Linear | C9 | 0.68 | 0.023 | 11.6 | 12.45 | 86 | 100 | 114 | 1262 | 156 | 0 | 0 |
| Diolefin | C7 | 1.13 | 0.011 | 7.2 | 9 | 96 | 0 | 0 | 0 | 0 | 0 | 0 |
| Diolefin | C8 | 2.14 | 0.091 | 7.2 | 9.19 | 110 | 0 | 0 | 0 | 0 | 0 | 0 |
| Diolefin | C8 | 2.14 | 0.091 | 9.2 | 11.5 | 110 | 0 | 0 | 0 | 0 | 0 | 0 |
| Diolefin | C9 | 1.13 | 0.012 | 9 | 11 | 124 | 154 | 0 | 0 | 0 | 0 | 0 |
| Diolefin | C9 | 1.13 | 0.012 | 11.01 | 12.45 | 124 | 154 | 0 | 0 | 0 | 0 | 0 |
| Cyclic Olefin | C7 | 1.19 | 0.109 | 7.2 | 8.9 | 95 | 0 | 0 | 0 | 0 | 0 | 0 |
| Cyclic Olefin | C8 | 2.20 | 0.022 | 7.2 | 9.7 | 109 | 0 | 0 | 0 | 0 | 0 | 0 |
| Cyclic Olefin | C8 | 2.20 | 0.022 | 9.7 | 11.5 | 109 | 0 | 0 | 0 | 0 | 0 | 0 |
| Cyclic Olefin | C9 | 0.60 | 0.197 | 10.3 | 12.45 | 123 | 0 | 0 | 0 | 0 | 0 | 0 |
| Cyclic Olefin | C7 | 1.17 | 0.001 | 7.4 | 8 | 94 | 0 | 0 | 0 | 0 | 0 | 0 |
| Cyclic Olefin | C8 | 1.27 | −0.012 | 8 | 12.3 | 108 | 0 | 0 | 0 | 0 | 0 | 0 |
| Mono Aromatic | C7 | 1.25 | 0.796 | 8.15 | 8.3 | 9.1 | 92 | 122 | 0 | 0 | 0 | 0 |
| Mono Aromatic | C8 | 1.13 | 1.054 | 10.7 | 11.7 | 105 | 106 | 136 | 0 | 0 | 0 | 0 |
| Mono Aromatic | C9 | 1.02 | 0.459 | 11.5 | 12.47 | 119 | 120 | 150 | 0 | 0 | 0 | 0 |

TABLE 5-continued

| Species | Carbon Number | Slope | Intercept | Ret Time Window | Mass 1 | Mass 2 | Mass 3 | Mass 4 | Mass 5 | Mass 6 | Mass 7 | Mass 0 |
|---|---|---|---|---|---|---|---|---|---|---|---|---|
| Thiophenes + Benzthio | C5 | 1.50 | 0.000 | 8 | + | 98 | 128 | 0 | 0 | 0 | 0 | 0 |
| Thiophenes + Benzthio | C6 | 4.26 | 0.065 | 10 | 12 | 112 | 142 | 0 | 0 | 0 | 0 | 0 |

TABLE 6

Individual Species Homologues for Boiling Range 154–182° C.

| Species | Carbon Number | Slope | Intercept | Ret Time Window Low | Ret Time Window High | Mass 1 | Mass 2 | Mass 3 | Mass 4 | Mass 5 | Mass 6 | Mass 7 |
|---|---|---|---|---|---|---|---|---|---|---|---|---|
| Paraffin ISO | C10 | 0.51 | 0.074 | 11.4 | 14.1 | 141 | 0 | 0 | 0 | 0 | 0 | 0 |
| Paraffin ISO | C11 | 0.61 | 0.014 | 13 | 15.05 | 155 | 0 | 0 | 0 | 0 | 0 | 0 |
| Paraffin Normal | C10 | 0.39 | 0.012 | 14.2 | 14.5 | 141 | 0 | 0 | 0 | 0 | 0 | 0 |
| Mono Cyclic | C9 | 1.57 | −0.0110 | 12.45 | 13 | 125 | 0 | 0 | 0 | 0 | 0 | 0 |
| Mono Cyclic | C10 | 0.93 | 0.074 | 12 | 15.05 | 139 | 0 | 0 | 0 | 0 | 0 | 0 |
| Mono Olefin Branch | C10 | 0.13 | 0.100 | 12.4 | 13.8 | 86 | 114 | 128 | 140 | 170 | 0 | 0 |
| Mono Olefin Branch | C10 | 0.13 | 0.100 | 14.2 | 14.7 | 86 | 114 | 128 | 140 | 170 | 0 | 0 |
| Mono Olefin Branch | C11 | 0.14 | 0.062 | 13.5 | 15.05 | 154 | 184 | 0 | 0 | 0 | 0 | 0 |
| Mono Olefin Linear | C10 | 0.81 | 0.002 | 13.8 | 14.2 | 86 | 114 | 128 | 140 | 170 | 0 | 0 |
| Diolefin | C9 | 1.13 | 0.012 | 12.45 | 13.5 | 124 | 0 | 0 | 0 | 0 | 0 | 0 |
| Diolefin | C10 | 1.11 | 0.006 | 12.45 | 15.05 | 138 | 0 | 0 | 0 | 0 | 0 | 0 |
| Diolefin | C11 | 1.06 | 0.004 | 14.7 | 15.05 | 152 | 0 | 0 | 0 | 0 | 0 | 0 |
| Cyclic Olefin | C9 | 0.60 | 0.197 | 12.45 | 13 | 123 | 0 | 0 | 0 | 0 | 0 | 0 |
| Cyclic Olefin | C10 | 0.89 | 0.041 | 12.45 | 15.05 | 137 | 0 | 0 | 0 | 0 | 0 | 0 |
| Mono Aromatic | C9 | 1.02 | 0.459 | 12.47 | 13 | 119 | 120 | 150 | 0 | 0 | 0 | 0 |
| Mono Aromatic | C10 | 0.86 | 0.214 | 13.8 | 15.05 | 133 | 134 | 164 | 0 | 0 | 0 | 0 |
| Indans | C9 | 1.10 | 0.092 | 13.9 | 14.05 | 116 | 117 | 118 | 148 | 0 | 0 | 0 |
| Dicyclic | C9 | 0.96 | 0.039 | 13 | 14.43 | 123 | 0 | 0 | 0 | 0 | 0 | 0 |
| Thiophenes + Benzthio | C7 | 5.00 | 0.100 | 12.7 | 14.5 | 126 | 156 | 0 | 0 | 0 | 0 | 0 |

TABLE 7

Individual Species Homologues for Boiling Range 182–204° C.

| Species | Carbon Number | Slope | Intercept | Ret Time Window Low | Ret Time Window High | Mass 1 | Mass 2 | Mass 3 | Mass 4 | Mass 5 | Mass 6 | Mass 7 |
|---|---|---|---|---|---|---|---|---|---|---|---|---|
| Paraffin ISO | C11 | 0.61 | 0.014 | 15.05 | 16 | 155 | 0 | 0 | 0 | 0 | 0 | 0 |
| Paraffin ISO | C12 | 0.45 | −0.005 | 15.5 | 17.2 | 169 | 0 | 0 | 0 | 0 | 0 | 0 |
| Paraffin Normal | C11 | 0.34 | 0.001 | 16.2 | 16.5 | 155 | 0 | 0 | 0 | 0 | 0 | 0 |
| Mono Cyclic | C10 | 0.93 | 0.074 | 15.05 | 15.2 | 139 | 0 | 0 | 0 | 0 | 0 | 0 |
| Mono Cyclic | C11 | 1.54 | −0.002 | 15.44 | 17.2 | 153 | 0 | 0 | 0 | 0 | 0 | 0 |
| Mono Olefin Branch | C11 | 0.14 | 0.062 | 15.05 | 16.7 | 154 | 184 | 0 | 0 | 0 | 0 | 0 |
| Mono Olefin Branch | C12 | 0.05 | 0.028 | 15.76 | 17.2 | 168 | 198 | 0 | 0 | 0 | 0 | 0 |
| Diolefin | C10 | 1.11 | 0.006 | 15.05 | 16.7 | 138 | 0 | 0 | 0 | 0 | 0 | 0 |
| Diolefin | C11 | 1.06 | 0.004 | 15.05 | 17.2 | 152 | 0 | 0 | 0 | 0 | 0 | 0 |
| Cyclic Olefin | C10 | 0.89 | 0.041 | 15.05 | 15.95 | 137 | 0 | 0 | 0 | 0 | 0 | 0 |
| Cyclic Olefin | C11 | 0.47 | 0.002 | 15.5 | 17.2 | 151 | 0 | 0 | 0 | 0 | 0 | 0 |
| Cyclic Olefin | C12 | 0.80 | 0.009 | 16.7 | 17.2 | 165 | 0 | 0 | 0 | 0 | 0 | 0 |
| Mono Aromatic | C10 | 0.86 | 0.214 | 15.1 | 17.1 | 133 | 134 | 164 | 0 | 0 | 0 | 0 |
| Mono Aromatic | C11 | 0.65 | 0.167 | 15 | 17.1 | 147 | 148 | 178 | 0 | 0 | 0 | 0 |
| Indans | C9 | 1.10 | 0.092 | 14.8 | 15.6 | 116 | 117 | 118 | 146 | 148 | 0 | 0 |
| Indans | C10 | 1.14 | 0.089 | 15.05 | 17.15 | 130 | 131 | 132 | 162 | 0 | 0 | 0 |
| Indans | C11 | 1.11 | 0.120 | 15.44 | 17.2 | 145 | 146 | 176 | 0 | 0 | 0 | 0 |
| Dicyclic | C10 | 0.55 | 0.005 | 15.95 | 16.8 | 137 | 0 | 0 | 0 | 0 | 0 | 0 |

TABLE 8

Individual Species Homologues for Boiling Range 204–232° C.

| Species | Carbon Number | Slope | Intercept | Ret Time Window Low | Ret Time Window High | Mass 1 | Mass 2 | Mass 3 | Mass 4 | Mass 5 | Mass 6 | Mass 7 |
|---|---|---|---|---|---|---|---|---|---|---|---|---|
| Paraffin ISO | C12 | 0.45 | −0.005 | 17.2 | 17.9 | 169 | 0 | 0 | 0 | 0 | 0 | 0 |
| Paraffin ISO | C13 | 0.56 | 0.020 | 17.2 | 19.5 | 183 | 0 | 0 | 0 | 0 | 0 | 0 |
| Paraffin ISO | C14 | 0.51 | 0.017 | 19.1 | 19.7 | 197 | 0 | 0 | 0 | 0 | 0 | 0 |
| Paraffin Normal | C12 | 0.22 | 0.005 | 18 | 18.4 | 169 | 0 | 0 | 0 | 0 | 0 | 0 |
| Mono Cyclic | C12 | 0.31 | 0.038 | 17.2 | 19 | 167 | 0 | 0 | 0 | 0 | 0 | 0 |
| Mono Cyclic | C13 | 1.07 | 0.017 | 18.6 | 19.7 | 181 | 0 | 0 | 0 | 0 | 0 | 0 |
| Mono Olefin Branch | C13 | 0.20 | 0.028 | 17.2 | 18.6 | 182 | 212 | 0 | 0 | 0 | 0 | 0 |
| Diolefin | C11 | 1.06 | 0.004 | 17.2 | 18.6 | 152 | 0 | 0 | 0 | 0 | 0 | 0 |
| Cyclic Olefin | C12 | 0.80 | 0.009 | 17.2 | 17.7 | 165 | 0 | 0 | 0 | 0 | 0 | 0 |
| Mono Aromatic | C10 | 0.86 | 0.214 | 17.1 | 17.6 | 133 | 134 | 164 | 0 | 0 | 0 | 0 |
| Mono Aromatic | C11 | 0.65 | 0.167 | 17.1 | 19 | 147 | 148 | 178 | 0 | 0 | 0 | 0 |
| Mono Aromatic | C12 | 0.51 | 0.044 | 17.5 | 19.8 | 161 | 162 | 192 | 0 | 0 | 0 | 0 |
| Mono Aromatic | C13 | 0.85 | 0.035 | 24.9 | 25 | 175 | 176 | 206 | 0 | 0 | 0 | 0 |
| Indans | C10 | 1.14 | 0.089 | 17.15 | 17.5 | 130 | 131 | 132 | 162 | 0 | 0 | 0 |
| Indans | C11 | 1.11 | 0.120 | 17.2 | 19.8 | 144 | 145 | 146 | 176 | 0 | 0 | 0 |
| Indans | C12 | 1.01 | 0.114 | 17.2 | 19.7 | 159 | 160 | 190 | 0 | 0 | 0 | 0 |
| Indans | C13 | 1.10 | 0.011 | 17.9 | 19.7 | 173 | 174 | 204 | 0 | 0 | 0 | 0 |
| Diaromatic | C10 | 2.40 | 0.005 | 17.7 | 18 | 128 | 0 | 0 | 0 | 0 | 0 | 0 |
| Diaromatic | C11 | 2.36 | 0.009 | 19.5 | 20.2 | 142 | 0 | 0 | 0 | 0 | 0 | 0 |
| Dicyclic | C11 | 0.64 | 0.010 | 17.2 | 18.6 | 151 | 0 | 0 | 0 | 0 | 0 | 0 |
| Dicyclic | C12 | 0.88 | 0.007 | 17.7 | 18.6 | 165 | 0 | 0 | 0 | 0 | 0 | 0 |
| Thiophenes + Benzthio | C8 | 6.57 | 0.153 | 17.7 | 18.1 | 134 | 0 | 0 | 0 | 0 | 0 | 0 |

TABLE 9

Individual Species Homologues for Boiling Range 232+ ° C.

| Species | Carbon Number | Slope | Intercept | Ret Time Window Low | Ret Time Window High | Mass 1 | Mass 2 | Mass 3 | Mass 4 | Mass 5 | Mass 6 | Mass 7 |
|---|---|---|---|---|---|---|---|---|---|---|---|---|
| Paraffin ISO | C14 | 0.51 | 0.017 | 19.7 | 21.2 | 197 | 0 | 0 | 0 | 0 | 0 | 0 |
| Paraffin ISO | C15 | 0.36 | 0.016 | 20.5 | 22.6 | 211 | 0 | 0 | 0 | 0 | 0 | 0 |
| Paraffin Normal | C13 | 0.23 | 0.004 | 19.65 | 20 | 183 | 0 | 0 | 0 | 0 | 0 | 0 |
| Paraffin Normal | C14 | 0.20 | 0.003 | 21.2 | 21.5 | 197 | 0 | 0 | 0 | 0 | 0 | 0 |
| Paraffin Normal | C15 | 0.18 | 0.004 | 22.6 | 23.05 | 211 | 0 | 0 | 0 | 0 | 0 | 0 |
| Mono Cyclic | C13 | 1.07 | 0.017 | 19.7 | 20.7 | 181 | 0 | 0 | 0 | 0 | 0 | 0 |
| Mono Cyclic | C14 | 1.04 | 0.022 | 19.7 | 22.5 | 195 | 0 | 0 | 0 | 0 | 0 | 0 |
| Mono Aromatic | C13 | 0.85 | 0.035 | 19.63 | 21.2 | 175 | 176 | 206 | 0 | 0 | 0 | 0 |
| Indans | C12 | 1.01 | 0.114 | 19.7 | 21.9 | 159 | 160 | 190 | 0 | 0 | 0 | 0 |
| Indans | C13 | 1.10 | 0.011 | 19.7 | 22 | 173 | 174 | 204 | 0 | 0 | 0 | 0 |
| Diaromatic | C12 | 2.31 | 0.009 | 21 | 22.3 | 156 | 0 | 0 | 0 | 0 | 0 | 0 |
| Thiophenes + Benzthio | C9 | 5.90 | 0.241 | 19.35 | 20.5 | 148 | 0 | 0 | 0 | 0 | 0 | 0 |
| Thiophenes + Benzthio | C10 | 1.72 | 0.002 | 20.4 | 22 | 162 | 0 | 0 | 0 | 0 | 0 | 0 |

Precision is determined by analysis of a QA gasoline on a daily basis using the instant method. A table of average values, standard deviation, and relative standard deviation for species and boiling range totals as determined by the analyses of this QA gasoline is presented in Table 10.

TABLE 10

| Species | Average | Standard Deviation | Percent Relative Standard Deviation |
|---|---|---|---|
| Paraffin ISO | 15.80 | 0.57 | 3.59 |
| Paraffin Normal | 2.22 | 0.18 | 8.27 |
| Mono Cyclic | 12.41 | 0.58 | 4.68 |
| Mono Olefin Branch | 14.37 | 0.50 | 3.48 |
| Mono Olefin Linear | 8.92 | 1.52 | 17.00 |
| Diolefin | 1.00 | 0.10 | 9.84 |
| Cyclic Olefin | 7.61 | 0.37 | 4.83 |
| Cyclic Diolefin | 0.21 | 0.06 | 25.92 |
| Mono Aromatic | 28.57 | 1.50 | 5.25 |
| Indans | 6.73 | 0.55 | 8.20 |
| Diaromatic | 1.74 | 0.19 | 10.91 |
| Dicyclic | 0.26 | 0.02 | 8.59 |
| Thiophenes | 0.15 | 0.02 | 14.53 |
| Boiling Ranges (° C.) | | | |
| 45–65.5 | 7.84 | 2.01 | 25.67 |
| 65.5–98.9 | 22.29 | 1.56 | 6.99 |
| 98.9–154 | 30.95 | 1.26 | 4.08 |

TABLE 10-continued

| Species | Average | Standard Deviation | Percent Relative Standard Deviation |
|---|---|---|---|
| 154–182 | 15.96 | 0.86 | 5.39 |
| 182–204 | 10.53 | 0.92 | 8.72 |
| 204–232 | 8.40 | 0.67 | 7.95 |
| 232+ | 4.03 | 0.85 | 21.12 |

Precision calculations are made for repetitive analyses of a QA gasoline sample. These results indicate that precision for components in the 5–45% concentration range generally have approximately 3–7% relative standard deviation. This QA sample is also used as a QC sample. If any of the values monitored fall out of the two sigma range, routine maintenance is undertaken to bring subsequent analyses of the QA sample into the two sigma range.

Tables 11 and 12 show a comparison of the analysis of select standard reference samples by this method, and by PIANO, DHAX, and ASTM Aromatics analyses. Table 11 shows totals by species and Table 12 shows totals by carbon number.

TABLE 11

A Comparison of Analyses Results for 4 MWK Gasolines

| Totals by Species wt % | TDNOCI GC/MS | PIANO | DHAX | ASTM AROMATICS Analyses |
|---|---|---|---|---|
| MWK A | | | | |
| n-Paraffins | 3.86 | 3.30 | 3.93 | |
| l-paraffins | 36.59 | 35.36 | 39.54 | |
| Olefins | 22.53 | 24.54 | 19.12 | |
| Naphthenes | 17.69 | 17.49 | 18.70 | |
| Aromatics | 19.33 | 19.31 | 18.71 | 17.93 |
| Total: | 100.00 | 100.00 | 100.00 | |
| MWK B | | | | |
| n-Paraffins | 3.09 | 1.87 | 4.31 | |
| l-paraffins | 11.85 | 15.85 | 23.06 | |
| Olefins | 55.63 | 51.46 | 40.83 | |
| Naphthenes | 13.89 | 15.05 | 16.38 | |
| Aromatics | 15.54 | 15.88 | 15.42 | 13.53 |
| Total: | 100.00 | 100.11 | 100.00 | |
| MWK C | | | | |
| n-Paraffins | 2.29 | 1.98 | 2.85 | |
| l-paraffins | 20.20 | 20.95 | 26.66 | |
| Olefins | 22.07 | 22.66 | 18.27 | |
| Naphthenes | 19.61 | 20.53 | 20.05 | |
| Aromatics | 35.84 | 33.87 | 32.17 | 31.82 |
| Total: | 100.00 | 99.99 | 100.00 | |
| MWK D | | | | |
| n-Paraffins | 2.37 | 2.67 | 3.68 | |
| l-paraffins | 28.25 | 26.46 | | |
| Olefins | 30.93 | 31.19 | 25.52 | |
| Naphthenes | 13.82 | 14.40 | 15.21 | |
| Aromatics | 24.63 | 25.17 | 24.35 | 23.99 |
| Total: | 100.00 | 99.89% | 100.00% | |

TABLE 12

| Totals by Carbon # Wt % | TDNOCI GC/MS | PIANO | DHAX |
|---|---|---|---|
| MWK A | | | |
| C5 | 5.07 | 5.98 | 6.02 |
| C6 | 25.62 | 26.36 | 24.24 |
| C7 | 30.97 | 30.61 | 31.57 |
| C8 | 27.07 | 25.99 | 27.05 |
| C9 | 8.60 | 9.54 | 8.83 |
| C10 | 1.06 | 1.21 | 2.11 |
| C11 | 0.63 | 0.22 | 0.18 |
| C12 | 0.64 | 0.07 | 0.00 |
| C13 | 0.27 | 0 | 0.00 |
| MWK B | | | |
| C5 | 4.91 | 3.72 | 5.13 |
| C6 | 24.72 | 27.07 | 22.42 |
| C7 | 30.66 | 29.14 | 30.45 |
| C8 | 24.18 | 26.26 | 27.40 |
| C9 | 12.04 | 11.08 | 12.02 |
| C10 | 1.35 | 1.71 | 2.28 |
| C11 | 0.79 | 0.21 | 0.26 |
| C12 | 0.87 | 0.30 | 0.03 |
| C13 | 0.34 | 0.48 | 0.00 |
| MWK C | | | |
| C5 | 3.86 | 4.75 | 4.87 |
| C6 | 24.25 | 24.57 | 22.53 |
| C7 | 29.75 | 30.67 | 31.65 |
| C8 | 28.92 | 28.89 | 30.63 |
| C9 | 9.45 | 9.26 | 5.89 |
| C10 | 1.76 | 1.25 | 4.07 |
| C11 | 0.83 | 0.21 | 0.34 |
| C12 | 0.76 | 0.16 | 0.03 |
| C13 | 0.33 | 0.25 | 0.00 |
| MWK D | * | | |
| C5 | 5.61 | 5.50 | 6.06 |
| C6 | 30.27 | 29.33 | 26.10 |
| C7 | 31.61 | 30.70 | 32.33 |
| C8 | 24.12 | 24.93 | 26.24 |
| C9 | 7.26 | 8.04 | 6.35 |
| C10 | 0.77 | 1.06 | 2.61 |
| C11 | 0.17 | 0.19 | 0.28 |
| C12 | 0.10 | 0.12 | 0.02 |
| C13 | 0.09 | 0.11 | 0.00 |

Table 13 shows an example of a typical final report format for the instant method.

TABLE 13

| Boiling range (° C.) | 45–65.5 wt % total = 5.8 | | | | 65–98.9 wt % total = 18.5 | | | | 98.9–154 wt % total = 33.2 | | | | | | |
|---|---|---|---|---|---|---|---|---|---|---|---|---|---|---|---|
| Species | C4 | C5 | C6 | Total | C4 | C6 | C7 | Total | C4 | C5 | C6 | C7 | C8 | C9 | Total |
| PARAFFIN ISO | 0.0 | 8.5 | 45.2 | 53.7 | 0.0 | 0.0 | 17.1 | 17.1 | 0.0 | 0.0 | 0.0 | 0.0 | 9.2 | 7.6 | 16.9 |
| PARAFFIN NORMAL | 0.0 | 0.0 | 0.0 | 0.0 | 0.0 | 1.9 | 2.1 | 4.0 | 0.0 | 0.0 | 0.0 | 0.0 | 1.3 | 1.2 | 2.6 |

TABLE 13-continued

| Species | | | | | | | | | | | | | | | |
|---|---|---|---|---|---|---|---|---|---|---|---|---|---|---|---|
| MONO CYCLIC | 0.0 | 0.0 | 0.0 | 0.0 | 0.0 | 8.3 | 4.5 | 12.9 | 0.0 | 0.0 | 0.0 | 3.1 | 9.0 | 4.7 | 16.8 |
| MONO OLEFIN BRANCH | 0.0 | 18.2 | 12.0 | 30.2 | 0.0 | 16.7 | 20.2 | 37.0 | 0.0 | 0.0 | 0.0 | 5.2 | 3.3 | 8.5 |  |
| MONO OLEFIN LINEAR | 0.0 | 8.1 | 5.3 | 13.4 | 0.0 | 4.8 | 7.2 | 12.0 | 0.0 | 0.0 | 0.0 | 1.7 | 0.6 | 2.4 |  |
| DIOLEFIN | 0.0 | 0.0 | 0.0 | 0.0 | 0.0 | 0.7 | 0.0 | 0.7 | 0.0 | 0.0 | 0.0 | 0.8 | 0.2 | 0.3 | 1.2 |
| CYCLIC OLEFIN | 0.0 | 2.7 | 0.0 | 2.7 | 0.0 | 7.7 | 4.8 | 12.5 | 0.0 | 0.0 | 0.0 | 3.6 | 1.9 | 0.9 | 6.5 |
| CYCLIC DIOLEFIN | 0.0 | 0.0 | 0.0 | 0.0 | 0.0 | 0.2 | 0.0 | 0.2 | 0.0 | 0.0 | 0.0 | 0.1 | 0.3 | 0.0 | 0.4 |
| MONO AROMATIC | 0.0 | 0.0 | 0.0 | 0.0 | 0.0 | 3.7 | 0.0 | 3.7 | 0.0 | 0.0 | 0.0 | 14.1 | 30.1 | 0.3 | 44.5 |
| INDANS | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| DIAROMATIC | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| DICYCLIC | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Thiophenes | 0.0 | 0.0 | 0.0 | 0.0 | 0.0 | 0.0 | 0.0 | 0.0 | 0.3 | 0.0 | 0.0 | 0.0 | 0.0 | 0.0 | 0.3 |
| Total | 0.0 | 37.5 | 62.5 | 100.0 | 0.0 | 44.1 | 55.9 | 100.0 | 0.0 | 0.3 | 0.0 | 21.7 | 58.9 | 19.1 | 100.0 |

| Boiling range (° C.) | Summed and Renormalized 45–154 | | | | | | |
|---|---|---|---|---|---|---|---|
| Species | C4 | C5 | C6 | C7 | C8 | C9 | Total |
| PARAFFIN ISO | 0.0 | 0.9 | 4.5 | 5.5 | 5.3 | 4.4 | 20.6 |
| PARAFFIN NORMAL | 0.0 | 0.0 | 0.6 | 0.7 | 0.8 | 0.7 | 2.8 |
| MONO CYCLIC | 0.0 | 0.0 | 2.7 | 3.3 | 5.2 | 2.7 | 13.9 |
| MONO OLEFIN BRANCH | 0.0 | 1.8 | 6.6 | 6.5 | 3.0 | 1.9 | 19.8 |
| MONO OLEFIN LINEAR | 0.0 | 0.8 | 2.1 | 2.3 | 1.0 | 0.4 | 6.6 |
| DIOLEFIN | 0.0 | 0.0 | 0.2 | 0.4 | 0.1 | 0.2 | 0.9 |
| CYCLIC OLEFIN | 0.0 | 0.3 | 2.5 | 3.6 | 1.1 | 0.5 | 8.1 |
| CYCLIC DIOLEFIN | 0.0 | 0.0 | 0.1 | 0.0 | 0.2 | 0.0 | 0.3 |
| MONO AROMATIC | 0.0 | 0.0 | 1.2 | 8.1 | 17.4 | 0.2 | 26.9 |
| INDANS | 0.0 | 0.0 | 0.0 | 0.0 | 0.0 | 0.0 | 0.0 |
| DIAROMATIC | 0.0 | 0.0 | 0.0 | 0.0 | 0.0 | 0.0 | 0.0 |
| DICYCLIC | 0.0 | 0.0 | 0.0 | 0.0 | 0.0 | 0.0 | 0.0 |
| Thiophenes | 0.0 | 0.2 | 0.0 | 0.0 | 0.0 | 0.0 | 0.2 |
| Total | 0.0 | 3.9 | 20.5 | 30.5 | 34.1 | 11.0 | 100.0 |

| Boiling range | 154–182 wt % total = 17.6 | | | | | 182–204 wt % total = 11.6 | | | | | 204–232 wt % total = 11.4 | | | | | |
|---|---|---|---|---|---|---|---|---|---|---|---|---|---|---|---|---|
| Species | C7 | C9 | C10 | C11 | Total | C9 | C10 | C11 | C12 | Total | C8S | C10 | C11 | C12 | C13 | C14 | Total |
| PARAFFIN ISO | 0.0 | 0.0 | 10.9 | 2.2 | 13.1 | 0.0 | 0.0 | 5.2 | 2.4 | 7.6 | 0.0 | 0.0 | 0.0 | 3.3 | 3.5 | 0.2 | 7.1 |
| PARAFFIN NORMAL | 0.0 | 0.0 | 2.5 | 0.0 | 2.5 | 0.0 | 0.0 | 3.0 | 0.0 | 3.0 | 0.0 | 0.0 | 0.0 | 3.8 | 0.0 | 0.0 | 3.8 |
| MONO CYCLIC | 0.0 | 0.8 | 5.0 | 0.0 | 5.8 | 0.0 | 0.0 | 0.2 | 1.3 | 0.0 | 1.5 | 0.0 | 0.0 | 0.0 | 2.5 | 0.4 | 0.0 | 2.9 |
| MONO OLEFIN BRANCH | 0.0 | 0.0 | 2.4 | 0.3 | 2.8 | 0.0 | 0.0 | 0.8 | 0.0 | 0.8 | 0.0 | 0.0 | 0.0 | 0.0 | 0.0 | 0.0 | 0.0 |
| MONO OLEFIN LINEAR | 0.0 | 0.0 | 0.3 | 0.0 | 0.3 | 0.0 | 0.0 | 0.0 | 0.0 | 0.0 | 0.0 | 0.0 | 0.0 | 0.0 | 0.0 | 0.0 | 0.0 |
| DIOLEFIN | 0.0 | 0.2 | 0.1 | 0.0 | 0.3 | 0.0 | 0.0 | 0.0 | 0.0 | 0.1 | 0.0 | 0.0 | 0.0 | 0.0 | 0.0 | 0.0 | 0.0 |
| CYCLIC OLEFIN | 0.0 | 0.9 | 0.9 | 0.0 | 1.8 | 0.0 | 0.0 | 0.4 | 1.3 | 0.1 | 1.8 | 0.0 | 0.0 | 0.0 | 0.1 | 0.0 | 0.0 | 0.1 |
| CYCLIC DIOLEFIN | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| MONO AROMATIC | 0.0 | 71.3 | 1.4 | 0.0 | 72.7 | 0.0 | 49.9 | 8.7 | 0.0 | 58.6 | 0.0 | 2.8 | 20.4 | 12.3 | 0.0 | 0.0 | 35.4 |
| INDANS | 0.0 | 0.1 | 0.0 | 0.0 | 0.1 | 9.5 | 15.5 | 1.5 | 0.0 | 26.5 | 0.0 | 9.8 | 19.4 | 3.9 | 0.2 | 0.0 | 33.3 |
| DIAROMATIC | 0.0 | 0.0 | 0.0 | 0.0 | 0.0 | 0.0 | 0.0 | 0.0 | 0.0 | 0.0 | 0.0 | 8.7 | 8.0 | 0.0 | 0.0 | 0.0 | 16.7 |
| DICYCLIC | 0.0 | 0.6 | 0.0 | 0.0 | 0.6 | 0.0 | 0.0 | 0.0 | 0.0 | 0.0 | 0.0 | 0.0 | 0.1 | 0.2 | 0.0 | 0.0 | 0.3 |
| Thiophenes | 0.0 | 0.0 | 0.0 | 0.0 | 0.0 | 0.0 | 0.0 | 0.0 | 0.0 | 0.0 | 0.4 | 0.0 | 0.0 | 0.0 | 0.0 | 0.0 | 0.4 |
| Total | 0.0 | 73.9 | 23.5 | 2.5 | 100.0 | 9.5 | 66.1 | 21.9 | 2.5 | 100.0 | 0.4 | 21.2 | 48.0 | 26.1 | 4.0 | 0.2 | 100.0 |

| Boiling range | 232+ wt % total = 2.0 | | | | | | | Boiling Ranges | % wt |
|---|---|---|---|---|---|---|---|---|---|
| Species | C9S | C10S | C12 | C13 | C14 | C15 | Total | | |
| PARAFFIN ISO | 0.0 | 0.0 | 0.0 | 0.0 | 11.4 | 0.0 | 11.4 | 45–65.5 | 5.8 |
| PARAFFIN NORMAL | 0.0 | 0.0 | 0.0 | 47.8 | 0.0 | 0.0 | 47.8 | 65.5–98.9 | 18.5 |
| MONO CYCLIC | 0.0 | 0.0 | 0.0 | 2.5 | 0.6 | 0.0 | 3.0 | 98.9–154 | 33.2 |
| MONO OLEFIN BRANCH | 0.0 | 0.0 | 0.0 | 0.0 | 0.0 | 0.0 | 0.0 | 154–182 | 17.6 |
| MONO OLEFIN LINEAR | 0.0 | 0.0 | 0.0 | 0.0 | 0.0 | 0.0 | 0.0 | 182–204 | 11.6 |
| DIOLEFIN | 0.0 | 0.0 | 0.0 | 0.0 | 0.0 | 0.0 | 0.0 | 204–232 | 11.4 |
| CYCLIC OLEFIN | 0.0 | 0.0 | 0.0 | 0.0 | 0.0 | 0.0 | 0.0 | 232+ | 2.0 |
| CYCLIC DIOLEFIN | 0.0 | 0.0 | 0.0 | 0.0 | 0.0 | 0.0 | 0.0 | Total | 100.0 |
| MONO AROMATIC | 0.0 | 0.0 | 0.0 | 7.0 | 0.0 | 0.0 | 7.0 | | |
| INDANS | 0.0 | 0.0 | 19.4 | 2.9 | 0.0 | 0.0 | 22.4 | | |
| DIAROMATIC | 0.0 | 0.0 | 0.0 | 0.0 | 0.0 | 0.0 | 0.0 | | |
| DICYCLIC | 0.0 | 0.0 | 0.0 | 0.0 | 0.0 | 0.0 | 0.0 | | |
| Thiophenes | 8.3 | 0.1 | 0.0 | 0.0 | 0.0 | 0.0 | 8.3 | | |
| Total | 8.3 | 0.1 | 19.4 | 60.3 | 12.0 | 0.0 | 100.0 | | |

| By Species | Totals wt % By Carbon # | Thiophenes and benzthiophenes Totals wt % |
|---|---|---|

TABLE 13-continued

| | | | | | |
|---|---|---|---|---|---|
| PARAFFIN ISO | 15.9 | C4 | 0.0 | C4 | 0.0 |
| PARAFFIN NORMAL | 3.3 | C5 | 2.2 | C5 | 0.1 |
| MONO CYCLIC | 9.4 | C6 | 12.5 | C6 | 0.0 |
| MONO OLEFIN BRANCH | 12.4 | C7 | 18.1 | C7 | 0.0 |
| MONO OLEFIN LINEAR | 4.0 | C8 | 18.6 | C8 | 0.1 |
| DIOLEFIN | 0.6 | C9 | 18.8 | C9 | 0.1 |
| CYCLIC OLEFIN | 5.3 | C10 | 15.2 | C10 | 0.0 |
| CYCLIC DIOLEFIN | 0.2 | C11 | 9.5 | Total | 0.2 |
| MONO AROMATIC | 38.4 | C12 | 3.9 | | |
| INDANS | 8.1 | C13 | 1.1 | | |
| DIAROMATIC | 2.1 | C14 | 0.1 | | |
| DICYCLIC | 0.1 | C15 | 0.0 | | |
| Thiophenes | 0.2 | Total | 100.0 | | |
| Total | 100.0 | | | | |

TABLE 14

A Comparison of TDNOCI GC/MS, SIMDIST, and Distillation Data for Boiling Range wt %

TDNOCI GC/MS DATA

| Boiling Ranges (° C.) | Sample: A | B | C | D | E | F |
|---|---|---|---|---|---|---|
| 45–65.5 | 5.8 | 8.9 | 10.8 | 10.3 | 5.6 | 4.6 |
| 65.5–98.9 | 18.5 | 19.1 | 20.3 | 19.2 | 19.7 | 22.9 |
| 98.9–154 | 33.2 | 31.1 | 30.9 | 30.8 | 35.7 | 29.2 |
| 154–182 | 17.6 | 17.0 | 17.0 | 18.2 | 16.2 | 15.7 |
| 182–204 | 11.6 | 10.9 | 10.5 | 10.6 | 8.9 | 11.6 |
| 204–232 | 13.4 | 13.0 | 10.5 | 10.9 | 14.0 | 16.0 |
| Total: | 100.0 | 100.0 | 100.0 | 100.0 | 100.0 | 100.0 |

Measured SYMDIST Data

| Boiling Ranges (° C.) | Sample: C | E | F |
|---|---|---|---|
| 45–65.5 | 8.6 | 4.7 | 3.5 |
| 65.5–98.9 | 18.5 | 15.7 | 18.2 |
| 98.9–154 | 34 | 35.4 | 31.5 |
| 154–182 | 17.8 | 16.7 | 16.8 |
| 182–204 | 11.2 | 11.3 | 13.5 |
| 204–232 | 9.9 | 16.2 | 16.5 |
| Total: | 100.0 | 100.0 | 100.0 |

Distillation Cut Data

| Boiling Ranges (° C.) | Sample: A | B | C | D | E | F |
|---|---|---|---|---|---|---|
| 45–65.5 | 6.5 | 9.2 | 18.9 | 11.8 | 8.4 | 7.8 |
| 65.5–98.9 | 18.6 | 22.3 | 14.7 | 16.9 | 17.4 | 19.3 |
| 98.9–154 | 32.7 | 30.7 | 31.4 | 34.0 | 33.2 | 29.7 |
| 154–182 | 17.3 | 16.0 | 16.8 | 15.9 | 15.7 | 15.8 |
| 182–204 | 11.7 | 10.0 | 9.5 | 10.6 | 10.0 | 11.9 |
| 204–232 | 13.3 | 11.8 | 8.7 | 10.8 | 15.3 | 15.5 |
| Total: | 100.0 | 100.0 | 100.0 | 100.0 | 100.0 | 100.0 |

We claim:

1. A method of operating a calibrated gas chromatograph/mass spectrometer system for analysis of the chemical and physical properties of a complex mixture of hydrocarbons with a boiling range between about 10° C. and about 705° C., said complex mixture of hydrocarbons comprising gasoline and olefins, which method includes hydrocarbon speciation in the boiling range between about 23° C. and about 260° C., said method comprising:

introducing a sample of the complex mixture of hydrocarbons into the gas chromatograph to (partially) separate the mixture into its constituent components;

ionizing the resulting components via Townsend discharge nitric oxide chemical ionization;

introducing the resulting ionized components into the mass spectrometer to produce corresponding mass spectra; and, measuring, from the resulting mass spectra, the concentrations of individual hydrocarbon species and structural types comprising n-paraffins, iso-paraffins, cyclics, branched mono olefins, linear mono olefins, diolefins, cyclic olefins, cyclic diolefins, mono aromatics, indane/indenes, diaromatics, dicyclics, and benzothiophenes/dibenzothiophenes with in certain boiling ranges.

2. The method of claim 1 in which the mass spectrometer is a quadrupole mass spectrometer.

3. The method of claim 1 in which the sample of the complex mixture of hydrocarbons is selected from the group consisting of full range gasoline, gasoline fractions, distillation cuts and total liquid products.

4. The method of claim 1 in which the boiling ranges measured comprise: about 45° C. to about 65° C., about 65° C. to about 99° C., about 99° C. to about 154° C., about 154° C. to about 182° C., about 182° C. to about 204° C., about 204° C. to about 232° C., and about 232° C. to about 260° C.

5. The method of claim 1 in which the concentrations of the specified individual hydrocarbon species and structural types are measured by the following method comprising:

calibrating the GC/MS according to the standard procedure of the GC/MS; analyzing each standard repeatedly;

calculating a slope and a y-intercept for each homologue of each individual species from an averaged area percent value along with a weight percent value;

calculating concentrations from measured area percent values, according to Formula IV $$[(\text{If (Y-intercept)}>0, \text{(Y-intercept)},0))/\text{slope}] = X \quad (IV)$$

where Y is the area percent and X is the weight percent of a specific species homologue with respective slope and intercept;

analyzing the hydrocarbon sample using the GC/MS to produce a spectrum;

correcting the spectrum for the naturally occurring carbon-13 contribution from the lower mass ion; and, performing sample calculations using the method comprising:
   determining the areas for each of the individual species homologue retention windows by integrating the areas under the ion chromatogram and comparing to the standards.

6. The method of claim 5 in which the mass spectrometer is a quadrupole mass spectrometer.

7. The method of claim 5 in which the sample of the complex mixture of hydrocarbons is selected from the group consisting of full range gasoline, gasoline fractions, distillation cuts and total liquid products.

8. The method of claim 5 in which the boiling ranges measured comprise: about 45° C. to about 65° C., about 65° C. to about 99° C., about 99° C. to about 154° C., about 154° C. to about 182° C., about 182° C. to about 204° C., about 204° C. to about 232° C., and about 232° C. to about 260° C.

9. The method of claim 5 further comprising:
   measuring precision;
   measuring accuracy; and,
   checking quality control.

* * * * *